(12) United States Patent
Ustav et al.

(10) Patent No.: US 7,261,895 B2
(45) Date of Patent: Aug. 28, 2007

(54) PEPTIDE TAG FOR MONITORING AND PURIFICATION OF PROTEINS

(75) Inventors: Mart Ustav, Tartu (EE); Reet Kurg, Tartu (EE); Niilo Kaldalu, Tartu (EE)

(73) Assignee: Quattromed Ltd., Tartu (EE)

( * ) Notice: Subject to any disclaimer, the term of this patent is extended or adjusted under 35 U.S.C. 154(b) by 89 days.

(21) Appl. No.: 10/258,480

(22) PCT Filed: Feb. 26, 2001

(86) PCT No.: PCT/EE01/00001

§ 371 (c)(1),
(2), (4) Date: Mar. 21, 2003

(87) PCT Pub. No.: WO02/068460

PCT Pub. Date: Sep. 6, 2002

(65) Prior Publication Data

US 2003/0170615 A1    Sep. 11, 2003

(51) Int. Cl.
*A61K 39/00* (2006.01)
(52) U.S. Cl. .............................. 424/184.1; 424/192.1
(58) Field of Classification Search ................. 435/7.1, 435/339, 320.1, 5; 436/501; 536/23.4, 23.72; 530/350, 413, 387.9, 388.1, 389.4, 300, 387.1, 530/388.3; 424/204.1
See application file for complete search history.

(56) References Cited

U.S. PATENT DOCUMENTS 5,674,835 A * 10/1997 Androphy et al. .............. 514/2
5,679,543 A * 10/1997 Lawlis ....................... 435/69.1
5,989,868 A * 11/1999 Harrison et al. ........... 435/69.7

OTHER PUBLICATIONS

Kurg et al. Journal of Virology. Jun. 1999; 73 (6): 4670-4677.*
Sheibani. Preparative biochemistry and biotechnology. 1999; 29 (1): 77-90, abstract only.*
Kaldalu et al., "Monitoring and Purification of Proteins Using Bovine Papillomavirus E2 Epitope Tags", *BioTechniques*, vol. 28, No. 3, Mar. 2000, pp. 456-462, XP-002187757.
Giri et al., "Structural and Mutational Analysis of E2 Trans-Activating Proteins of Papillomaviruses Reveals Three Distinct Functional Domains," *The EMBO Journal*, vol. 7. No. 9, pp. 2823-2929, 1988.
Iives et al., "Long-Term Episomal Maintenance of Bovine Papillomavirus Type 1 Plasmids Is Determined by Attachment to Host Chromosomes, Which Is Mediated by the Viral E2 Protein and Its Binding Sites," *Journal of Virology*, vol. 72, No. 5, pp. 4404-4412, 1999.
Jarvik et al., "Epitope Tagging," *Annu. Rev. Genet*, vol. 32, pp. 601-618, 1998.
Juronen et al., "FPLC Purification of Mouse Monoclonal Antibodies from Ascitic Fluid Using Blue DEAE and Thiophilic Sorbents," *Journal of Immunological Methods*, vol. 136, pp. 103-109, 1991.
Kaldalu et al., "TOL Plasmid Transcription Factor XyIS Binds Specifically to the *PM* Operator Sequences," *Molecular Microbiology*, vol. 20, No. 3, pp. 569-579, 1996.
Kaldalu et al., "Functional Domains of the TOL Plasmid Transcription Factor XyIS," *Journal of Bacteriology*, vol. 182, No. 4, pp. 1118-1126, 2000.
Koljak et al., "The Basis of Prostaglandin Synthesis in Coral," *The Journal of Biological Chemistry*, vol. 276, No. 10, pp. 7033-7040, 2001.
Kurg et al., "Effect of Bovine Papillomavirus E2 Protein-Specific Monoclonal Antibodies on Papillomavirus DNA Replication," *Journal of Virology*, vol. 73, No. 6, pp. 4670-4677, 1999.
Langel et al., "Design of Chimeric Peptide Ligands to Galanin Receptors and Substance P Receptors," *Int. J. Peptide Protein Res.*, vol. 39, pp. 516-522, 1992.
Lepik et al., "p53 Protein Is a Suppressor of Papillomavirus DNA Amplificational Replication," *Journal of Virology*, vol. 72, NO. 8, pp. 6822-6831, 1998.
Piirsoo et al., "*Cis* and *Trans* Requirements for Stable Episomal Maintenance of the BPV-1 Replicator," *The EMBO Journal*, vol. 15, No. 1, pp. 1-11, 1996.
Sedman et al., "Binding of the E1 and E2 Proteins to the Origin of Replication of Bovine Papillomavirus," *Journal of Virology*, vol. 71, No. 4, pp. 2887-2896, 1997.
Spalholtz et al., "Transactivation of a Bovine Papilloma Virus Transcriptional Regulatory Element by the E2 Gene Product," *Cell*, vol. 42, pp. 183-191, 1985.
Tanaka et al., "Differential Transcriptional Activation by Oct. 1 and Oct. 2: Interdependent Activation Domains Induce Oct. 2 Phosphorylation," *Cell*, vol. 60, pp. 375-386, 1990.
Trifan et al., "Overexpression of Cycloosygenase-2 Induces Cell Cycle Arrest," *J. Biol. Chem*, vol. 274, Issue 48, pp. 34141-34147, 1999.
Ustav et al., "Transient Replication of BPV-1 Requires Two Viral Polypeptides Encoded by the E1 and E2 Open Reading Frames," *The EMBO Journal*, vol. 10, No. 2, pp. 449-457, 1991.

* cited by examiner

*Primary Examiner*—Bruce R. Campell
*Assistant Examiner*—Nicole E Kinsey
(74) *Attorney, Agent, or Firm*—Dodds and Associates; Susanne Somersalo; John Dodds

(57) ABSTRACT

This invention is concerned with a peptide tag having sequence SSTSSDFRDR or GVSSTSSDFRDR derived from transactivator protein E2 of Bovine Papillomavirus type 1, and the fusion polypeptide containing said peptide tag, and the expression vector comprising the oligonucleotide sequence encoding said peptide tag. The invention relates also to the antibodies specific for the peptide tag and the methods for detecting and purifying tagged proteins.

18 Claims, 5 Drawing Sheets

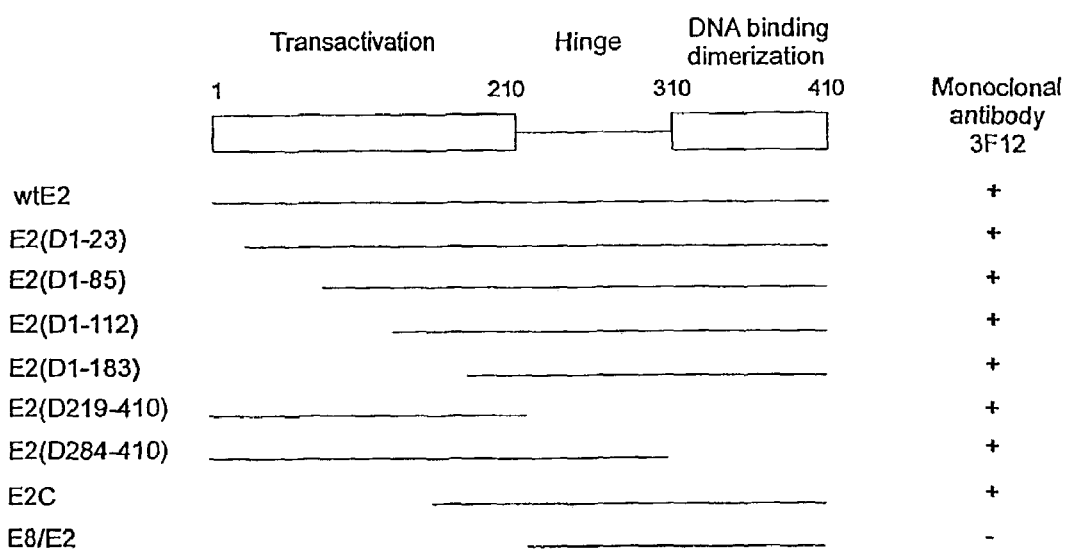
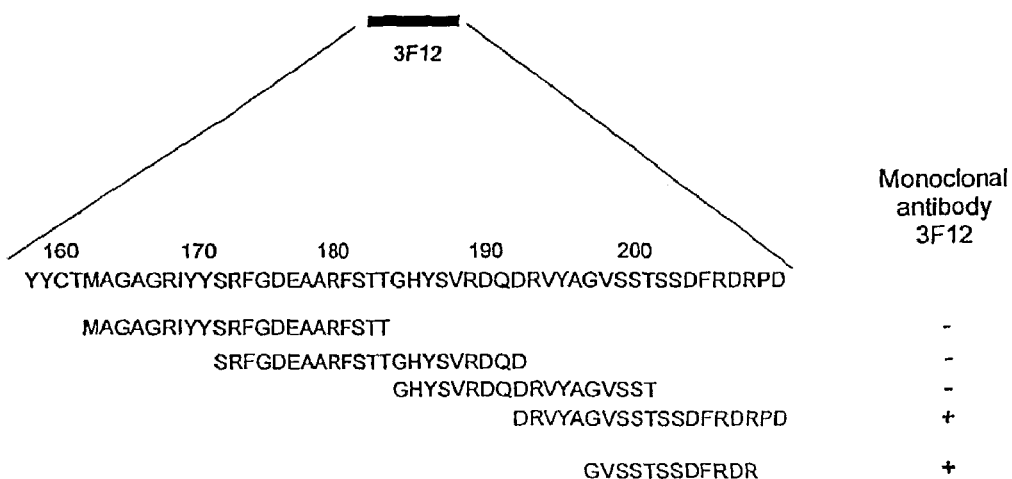
FIGURE 1

A
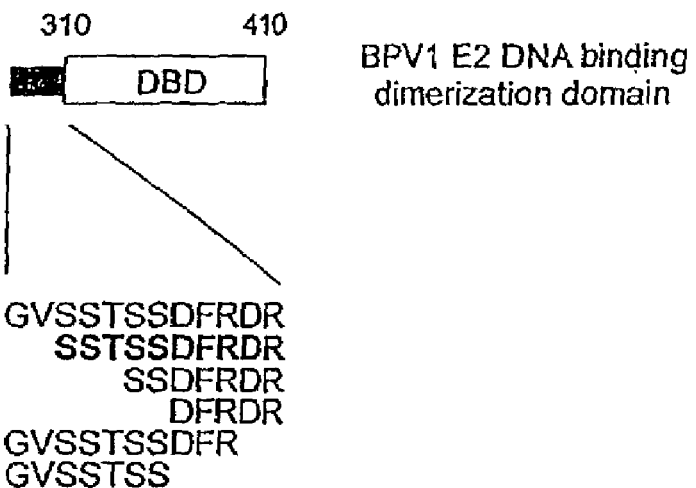
B
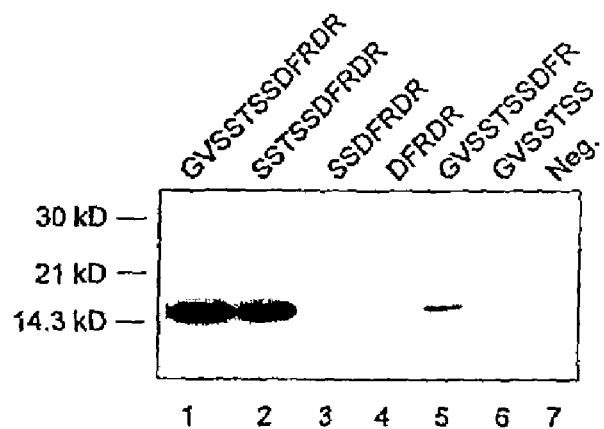
FIGURE 2

| Plasmid | Promoter | Tag location | 5' cloning site | Tag sequence | 3' cloning site |
|---|---|---|---|---|---|
| pBR-3F12 | Ptet | N-terminus | XbaI | M* G V S S T S S D F R D R S R...<br>5'-<u>CAT ATG</u> GGT GTC TCA TCC ACC TCT TCT GAT TTT AGA GAT CGC <u>TCT AGA</u>-3'<br>    *NdeI*                                                                                     *XbaI* | BamHI |
| pBR-NC | Ptet | N-terminus 1E2<br><br>C-terminus 3F12 | XbaI | M* T T G H Y S V R D S R...<br>5'-<u>CAT ATG</u> ACA ACA GGG CAT TAC TCT GTA AGA GAT <u>TCT AGA</u>-3'...<br>    *NdeI*                                                 *XbaI*<br>...G T S S D F R D R STOP<br>...5'-<u>GGT ACC</u> TCT TCT GAT TTT AGA GAT CGC TGA <u>GGA TCC</u>-3'<br>     *KpnI*                                               *BamHI* | KpnI[1] |
| pET-3F12 | T7 | N-terminus | XbaI | M* G V S S T S S D F R D R S R...<br>5'-<u>CAT ATG</u> GGT GTC TCA TCC ACC TCT TCT GAT TTT AGA GAT CGC <u>TCT AGA</u>-3'<br>    *NdeI*                                                                       *XbaI* | BamHI |
| pCG-3F12 | CMV IE | N- or C-terminus | BamHI<br>HindIII<br>SmaI<br>PstI<br>KpnI | M* G V S S T S S D F R D R...<br>5'-<u>TCT AGA</u> ATG GGT GTC TCA <u>AGT ACT</u> TCT TCT GAT TTT AGA GAT CGC...<br>    *XbaI*                        *ScaI*<br>...G A K L P G L Q G T R S<br>...<u>GGA TCC</u> <u>AAG CTT</u> <u>CCC GGG</u> <u>CTG CAG</u> <u>GGT ACC</u> <u>AGA TCT</u><br>    *BamHI*   *HindIII*  *SmaI*    *PstI*    *KpnI*    *BglII* | HindIII<br>SmaI<br>PstI<br>KpnI<br>BglII |

In amino acid sequences, the epitopes are underlined and the initiator methionine codons are marked with asterisks
In nucleotide sequences, cleaving sites for restriction endonucleases are underlined.
Restriction enzymes which cut once per plasmid are marked in bold.

FIGURE 4

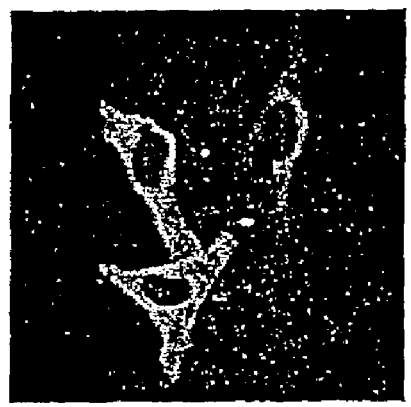 
FIGURE 5

SEQUENCE LISTING

<160> NUMBER OF SEQ ID NOS: 7

<210> SEQ ID NO 1
<211> LENGTH: 10
<212> TYPE: PRT
<213> ORGANISM: Bovine Papillomavirus type 1
<220> FEATURE:
<221> NAME/KEY: PEPTIDE
<222> LOCATION: (1)..(10)
<223> OTHER INFORMATION: Peptide Tag from E2 protein of Bovine
      Papillomavirus type 1

<400> SEQUENCE: 1

Ser Ser Thr Ser Ser Asp Phe Arg Asp Arg
1               5                   10

<210> SEQ ID NO 2
<211> LENGTH: 12
<212> TYPE: PRT
<213> ORGANISM: Bovine Papillomavirus type 1
<220> FEATURE:
<221> NAME/KEY: PEPTIDE
<222> LOCATION: (1)..(12)
<223> OTHER INFORMATION: Peptide tag from E2 protein of Bovine
      Papillomavirus type 1

<400> SEQUENCE: 2

Gly Val Ser Ser Thr Ser Ser Asp Phe Arg Asp Arg
1               5                   10

<210> SEQ ID NO 3
<211> LENGTH: 36
<212> TYPE: DNA
<213> ORGANISM: Bovine Paillomavirus type 1
<220> FEATURE:
<221> NAME/KEY: misc_feature
<222> LOCATION: (1)..(36)
<223> OTHER INFORMATION: DNA sequence encoding the peptide tag of SEQ ID
      NO:2 corresponding to Bovine PApillomavirus type 1 nucleotides
      3196-3231

<400> SEQUENCE: 3
ggtgtctcat ccacctcttc tgattttaga gatcgc                              36

<210> SEQ ID NO 4
<211> LENGTH: 36
<212> TYPE: DNA
<213> ORGANISM: Bovine papillomavirus type 1
<220> FEATURE:
<221> NAME/KEY: misc_feature
<222> LOCATION: (1)..(36)
<223> OTHER INFORMATION: Modified DNA sequence encoding the peptide tag
      of SEQ ID NO:2

<400> SEQUENCE: 4
ggtgtctcaa gtacttcttc tgattttaga gatcgc                              36

<210> SEQ ID NO 5
<211> LENGTH: 19
<212> TYPE: PRT
<213> ORGANISM: Bovine papillomavirus type 1
<220> FEATURE:
<221> NAME/KEY: PEPTIDE
<222> LOCATION: (1)..(19)
<223> OTHER INFORMATION: Synthetic peptide corresponding to amino acid
      residues 192-210 of Bovine Papillomavirus type 1 E2 protein

<400> SEQUENCE: 5

```
Asp Arg Val Tyr Ala Gly Val Ser Ser Thr Ser Ser Asp Phe Arg Asp
1               5                   10                  15

Phe Pro Asp

<210> SEQ ID NO 6
<211> LENGTH: 9
<212> TYPE: PRT
<213> ORGANISM: Bovine papillomavirus type 1
<220> FEATURE:
<221> NAME/KEY: PEPTIDE
<222> LOCATION: (1)..(9)
<223> OTHER INFORMATION: Synthetic peptide recognized by the anti E2
      specific antibody 1E2

<400> SEQUENCE: 6

Thr Thr Gly His Tyr Ser Val Arg Asp
1               5

<210> SEQ ID NO 7
<211> LENGTH: 8
<212> TYPE: PRT
<213> ORGANISM: Bovine Papillomavirus type 1
<220> FEATURE:
<221> NAME/KEY: PEPTIDE
<222> LOCATION: (1)..(8)
<223> OTHER INFORMATION: Synthetic peptide recognized by monoclonal
      antibody 3F12

<400> SEQUENCE: 7

Thr Thr Ser Asp Phe Arg Asp Phe
1               5
```

PEPTIDE TAG FOR MONITORING AND PURIFICATION OF PROTEINS

CROSS REFERENCE TO RELATED APPLICATIONS

This non-provisional patent application claims priority date of the international application WO 02/068460 filed on Feb. 26, 2001.

SEQUENCE DATA

This application contains sequence data provided on a computer readable diskette and as a paper version. The paper version of the sequence data is identical to the data provided on the diskette.

FIELD OF THE INVENTION

This invention relates to the peptide from Bovine Papillomavirus E2 protein suitable for use in epitope tagging, and the nucleotide sequences that encode the peptide tag. The invention also extends to the fused polypeptide containing the said tag and to the antibodies specific for the peptide tag of the invention and the methods for using the peptide tag.

BACKGROUND OF THE INVENTION

The epitope tagging is the recombinant DNA method for making the gene product immunoreactive to an already existing antibody (Jarvik and Telmer, Annu. Rev. Genet. 32:601-618, 1998). Typically the process involves inserting the nucleotide sequence encoding the peptide tag into the gene of interest and expressing the gene in an appropriate host. The protein can then be detected and/or purified by virtue of its interaction with the antibody specific to the epitope tag. This approach can elucidate the size of the tagged protein as well as its abundance, cellular location, posttranslational modifications and interactions with other proteins. In particular, antibodies recognizing the peptide tag facilitate purification and/or isolation of tagged proteins.

The epitope tagging is widely used for detecting, characterizing and purifying proteins. The technique offers several advantages over alternative methods of detecting and purifying proteins. The epitope tagging saves the time and resources comparing with the traditional method of producing an antibody to the specific protein being studied. The small size of the epitope tag, which is usually 5-15 amino acids in length, generally has no effect on the biological function of the tagged protein. However, sometimes the epitope tag may interfere with the protein structure and function or the target protein sequence can influence the antigenicity of the epitope. For this reason, it is sometimes essential to develop epitope tags of different sequence characteristics (different net charges, hydrophobicity and side groups) to increase the chance of success in tagging applications.

To date there are number of the epitope tags commercially available. Often they are incorporated into the expression vectors for mammalian, insect, yeast or bacterial cells. A variety of epitope tags are available, including c-myc, FLAG, HA, His6, T7-Tag, HSV-Tag, Pk-Tag, VSV-Tag, Glu-Glu, BTag and S-Tag. Most epitopes that have been popular for the epitope tagging are highly charged (HA, c-myc, FLAG). Since one generally aims to place the tag in the external portion of the target protein, it is appropriate that the tag be charged rather that hydrophobic. However, the tag of extreme or inappropriate charge could cause the problems in some cases, for example, if a basic domain of a protein is tagged with an acidic sequence. The epitope tags without highly charged amino acids are T7-Tag and BTag. The present invention seeks to provide an alternative to the currently available epitope tags. The E2Tag consists of ten 10 amino acid residues, SSTSSDFRDR (SEQ ID No. 1). We have designated this sequence as E2Tag. All these ten amino acids are required and are sufficient for strong interaction with monoclonal antibody 3F12. The first half of the sequence consists of polar amino acids, and the second half contains charged amino acid residues resulting in very hydrophilic peptide. Such highly hydrophilic sequences have the strong antigenicity and are correspondingly likely to adopt a highly exposed conformation in the three-dimensional folding of a protein.

The Bovine Papillomavirus type 1 (BPV-1 E2) E2 protein is the master regulator of the viral life cycle—this protein modulates the transcription of viral genes (Spalholtz et al., Cell 42:183-191, 1985) and is responsible for the initiation of DNA replication (Ustav and Stenlund, EMBO J. 10:449-457, 1991) and for the stable maintenance of the viral genome (Piirsoo et al., EMBO J. 15:1-11, 1996; Ilves et al., J. Virol. 73:4404-4412, 1999). E2 is a sequence-specific DNA-binding protein, which is composed of three function-specific domains: the amino-terminal part (aa 1-200) is an activation domain for transcription and replication. It is followed by the unstructured hinge region and the carboxy-terminal DNA-binding and dimerization domain (aa 310-410) (Giri and Yaniv, EMBO J. 7:2823-2829, 1988). The protein is about 48 kDa and is 410 amino acid residues in length.

SUMMARY OF THE INVENTION

The present invention is concerned with a linear antigenic peptide from Bovine Papillomavirus E2 protein which functions as an epitope tag when linked to a protein of interest, peptide having the sequence SSTSSDFRDR (SEQ ID No. 1) or GVSSTSSDFRDR (SEQ ID No. 2). The invention also extends to the antibodies specific for the peptide tag and the methods for using the peptide tag.

In the major aspect the present invention provides the fusion protein comprising the protein linked to the peptide tag SSTSSDFRDR (SEQ ID No. 1) or GVSSTSSDFRDR (SEQ ID No. 2) derived from the transactivator protein E2 of Bovine Papillomavirus type 1, and wherein said peptide tag is reactive with an specific antibody. When expressed, the fusion protein is distinguishable from the native protein by the absence of the ability of the native protein to specifically bind to an antibody specific for the peptide tag. The peptide tag may be linked to the molecule of interest by any convenient means. The peptide tag of the invention may be located at any site in the desired protein, in the N-terminus, in the C-terminus or at any site within the sequence of the protein of interest. The invention extends to the fusion protein comprising the peptide tag SSTSSDFRDR (SEQ ID No. 1) or GVSSTSSDFRDR (SEQ ID No. 2), the protein of interest and one or more linking sequences of the amino acids interposed between the peptide tag and the protein of interest, said linking sequences being cleavable at the specific amino acid by the proteolytic agent.

In the other aspect present invention provides the antibodies capable of recognizing the peptide tag SSTSSDFRDR (SEQ ID No. 1) and GVSSTSSDFRDR (SEQ ID No. 2). Preferred antibody is the monoclonal antibody 3F12. The antibodies of the invention may be conjugated to an enzyme or other signal system, for example, the horseradish peroxidase, commonly used in the detection methods. The antibody of the invention may be coupled to the solid support. The invention extends to the hybridoma cells capable to produce the monoclonal antibodies recognizing the peptide tag SSTSSDFRDR (SEQ ID No. 1) and GVSSTSSDFRDR (SEQ ID No. 2).

In another aspect of this invention the nucleic acid sequence encoding the peptide tag SSTSSDFRDR (SEQ ID No. 1) or GVSSTSSDFRDR (SEQ ID No. 2) is disclosed. The nucleotide sequence, which codes for the peptide tag or codes for the fusion protein, which comprises a native protein fused to the peptide tag. The invention extends to the DNA expression vector comprising DNA coding for the fusion protein, which comprises the peptide tag of the invention, the protein of interest, and optionally the linking sequence of the amino acids between the peptide tag and the protein of interest being cleavable at the specific amino acid by the proteolytic agent. The invention also provides the expression vector comprising sequences coding for the peptide tag of the invention and having at least one cloning sites. The vector may have multiple cloning sites in three reading frames.

In yet another aspect of this invention, methods for producing of the fusion proteins and the methods for identifying the fusion protein comprising the peptide tag is disclosed. The method involves attaching the oligonucleotide to the coding sequence of the native protein to produce the fusion protein, which comprises the peptide tag, which is coded for by the oligonucleotide. In the further step of the method the DNA coding for the fusion protein is introduced into an appropriate host cells by transformation or by transfection and expressing the fusion protein. The host cell may be any suitable type of the cells, such as a bacterium or a eukaryotic cell such as yeast or a mammalian cell. The next step is the identifying of the fusion protein using an antibody binding to the peptide tag. Preferably, the antibody of the identifying step is the monoclonal antibody 3F12. In the preferred embodiment, the identifying step is immunoblot analysis, in another embodiment the immunofluorescence microscopy is used for the identifying and yet in another embodiment the immunoaffinity column is used for the identifying.

In yet another aspect of this invention the method for purifying of the fusion protein is disclosed. The present invention provides the method for purifying or isolating the fusion protein, which comprises the peptide tag of the present invention by the affinity chromatography. The affinity separation may be achieved by contacting the fusion protein with an immobilized antibody, especially the monoclonal antibody specific for the peptide tag of the present invention. Then, the purified protein may be used directly or cleaved from the peptide tag by the proteolytic agent.

In yet another aspect of this invention the kit for the epitope tagging is disclosed. The kit for the epitope tagging comprises antibodies specific for the peptide tag of the invention. In the further embodiment the kit comprise additionally the DNA expression vector comprising DNA coding for the peptide tag of the invention. In another embodiment the kit comprises the expression vector comprising the sequences coding for the peptide tag of the invention and having at least one cloning site. The vector may have multiple cloning sites in three reading frames.

BRIEF DESCRIPTION OF THE FIGURES

FIG. 1 Panel A shows the truncated BPV-1 E2 proteins used to map the epitope for the monoclonal antibody 3F12, and the results of the immunoblot analysis (diagram at right) of lysates of COS-7 cells transfected with E2 expression constructs. Panel B shows results of ELISA analysis of Mab 3F12 binding to overlapping synthetic peptides covering the region of amino acids from 162 to 210 of E2.

FIG. 2 Panel A shows the peptide tags of different length used to map the epitope for monoclonal antibody 3F12. These peptide tags were fused in frame in front of the DNA-binding-dimerization domain of BPV1 E2 protein and expressed in COS-7 cells. Panel B shows the results of Western blot analysis of the lysates of COS-7 cells.

FIG. 4 provides sequences and main characteristics of expression vectors used in this invention.

FIG. 5 shows the detection of tagged proteins. Panel A—Western blot analysis of tagged proteins. Lanes 1-6: $E.$ $coli$ DH5α cells producing tagged XylS protein, bearing pBR-3F12 (lanes 1 and 4), pBR-1E2 (lanes 2 and 5) and pBR-NC (lanes 3 and 6) derived expression plasmids. Lanes 7-12: $E.$ $coli$ BL21 (DE3) cells bearing pET-3F12 derived expression plasmids, producing the epitope-tagged p53 variants ΔN39ΔC362 (lanes 7 and 10), ΔN39ΔC362trp248 (lanes 8 and 11) and ΔN61ΔC362 (lanes 9 and 12). Lanes 13 and 14: Saos-2 cells transfected with pCG-3F12 derived expression plasmids producing the epitope-tagged GAPDH (lane 13) and GAPDH-NLS (lane 14). Lane 15: Saos-2 cells expressing untagged p53. pAb 240 is the p53 specific polyclonal antibody. Panel B shows subcellular localization of the epitope-tagged GAPDH and GAPDH-NLS proteins.

DETAILED DESCRIPTION OF THE INVENTION

Figure 3:
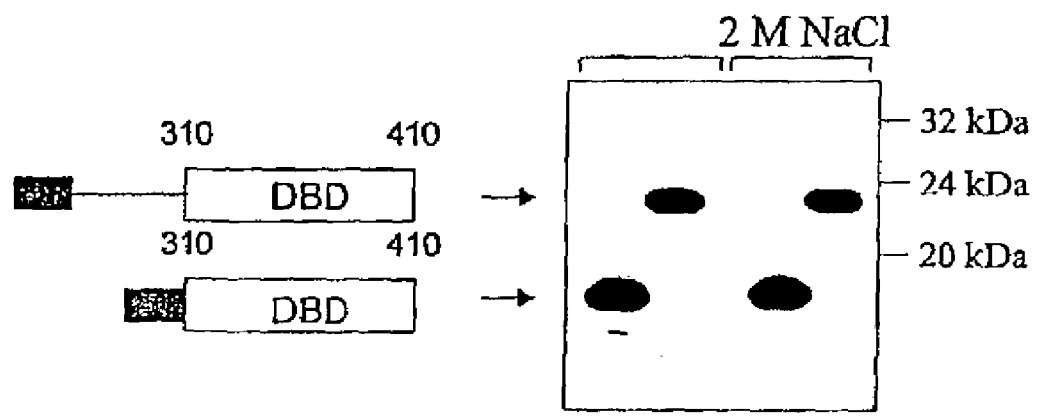
FIG. 3 shows that the monoclonal antibody 3F12 binds to the peptide tag in the presence of 2M NaCl. The grey box indicates the peptide tag SSTSSDFRDR (SEQ ID No. 1).

The practice of the present invention will employ, unless otherwise indicated, conventional molecular biology, immunology and recombinant DNA techniques within the skill of the art. Such techniques are explained fully in the literature, see Maniatis et al., Molecular Cloning: A Laboratory Manual (1982) and Harlow and Lane, Antibodies: A Laboratory Manual (1988).

The following terminology will be used in accordance with the definitions set out below in describing the present invention. As used herein, the term "peptide tag" is used to refer to peptides, such as SEQ ID No. 1 and SEQ ID No. 2, that are inserted into the protein. The peptide is inserted preferably in-frame into the nucleic acid encoding the protein as a piece of the nucleic acid encoding the peptide tag. As used herein, the term "epitope" means that portion of the recombinant protein that is recognized by the particular antibody. As used herein, the terms "fusion protein" or "fusion polypeptide" refer to the non-naturally occurring protein having the portion of the peptide tag and another portion of the protein which has been tagged. As used herein, the term "tagging" refers to introducing by recombinant methods one or more nucleotide sequences encoding a peptide tag into a polypeptide encoding gene. As used herein, the term "expression system" is well understood in the art to mean either in vitro system or cellular or multicellular organism capable for transcribing and translating the nucleotide sequences to produce the polypeptide.

The present invention relates to the use of the Bovine Papillomavirus E2 protein peptide fragment SSTSSDFRDR (SEQ ID No. 1) corresponding to the amino acid residues 199-208, and the antibodies binding to SEQ ID No. 1 for monitoring and purification of the proteins other than the viral E2 protein. The peptide sequence was identified using the monoclonal antibody, 3F12, that mapped to 10 residues in the E2 protein. Example 1 details the methods used to generate the antibodies against the BPV-1 E2 protein and Example 2 details the methods used to map antibody 3F12 to the peptide fragment on BPV-1 E2 protein.

Often the antibody to the particular protein is not available or the antibody to the protein does not bind specifically to that protein. In these cases, the antibody directed to the protein is not well suited for detecting and purification of the protein. The incorporation of SEQ ID No. 1 into the protein provides the suitable target for antibody binding. When incorporated into the protein, the antibodies recognizing the peptide tag SSTSSDFRDR (SEQ ID No. 1) can be used for monitoring or isolation the resulting fusion protein by any method that employs the antibody for isolation or detection of the protein. Examples of these methods include, but are not limited to, the immunoblotting including Western blotting, the immunofluorescence including traditional fluorescent microscopy, the inmmunoprecipitation, and/or the immuno-affinity chromatography.

In the first step of practicing of the invention it is obtained the fusion protein or polypeptide by addition of the linear amino acid sequence of SEQ ID No. 1 into the protein. There are a variety of methods for accomplishing this step. Usually, the incorporation of the peptide tag of SEQ ID No. 1 into the recombinant protein is achieved by the manipulation of nucleic acid encoding the protein. The epitope tags are added usually at the extreme N- or C-terminus of the protein, since the ends of the proteins are more likely to be accessible to the antibody, and the addition of the tag is less likely to affect the function of the protein, and because it is more convenient. Example 3 describes the fusion of the nucleic acid encoding the peptide tag of the invention to N- and C-terminus of several proteins. However, when the extreme ends of the protein are important for its function or when processing is taking place at these ends, then the internal tagging must be used. These methods use often the presence of suitable restriction endonuclease sites, the sequence encoding the peptide tag is added at the site of the existing restriction endonuclease recognition site or by blunt end ligation. When suitable restriction endonuclease sites are not available, one can use recombinant PCR methods to incorporate the tag into the internal portion of a protein. We have used internal tagging incorporating the peptide tag of the invention into the cyclooxygenase in Example 3.

In the present invention the oligonucleotide encoding the linear amino acid sequence SEQ ID No. 2 was incorporated into the different DNA expression vectors for moderate and high level bacterial expression and for eukaryotic expression of the epitope-tagged proteins. First the DNA sequence encoding the peptide tag of SEQ ID No. 2—GGT GTC TCA TCC ACC TCT TCT GAT TTT AGA GAT CGC (SEQ ID No. 3) corresponding to BPV-1 E2 nucleotides 3196-3231 (Bovine Papillomavirus type-1, complete genome, EMBL, accession No. X02346) was synthesized and incorporated into the bacterial expression vectors as described in Example 3. It is known that a number of different codons code for the same amino acid. The codon variations that result in the same amino acid are provided in the table form: p 214, Gene VI (by Lewin, 1997 Oxford University Press). To facilitate the cloning process we changed the nucleotide composition of the oligonucleotide to contain the restriction endonuclease site ScaI. Thus, the modified DNA sequence encoding the peptide tag of SEQ ID No. 2 used in some cases is GGT GTC TCA AGT ACT TCT TCT GAT TTT AGA GAT CGC (SEQ ID No. 4). Both sequences, SEQ ID No. 3 and SEQ ID No. 4 have been successfully used in tagging experiments (Example 3). All the expression vectors constructed—pBR-3F12, pBR-NC, pET-3F12 and pCG-3F12 contain unique restriction endonuclease sites to facilitate the cloning of the coding DNA sequence of the protein of interest.

The use of the tag to monitor or to purify the protein of interest requires the use of the antibody specific for the peptide sequence of SEQ ID No. 1. There are a variety of the methods for producing the monoclonal antibodies. Example 1 discloses methods used to produce the antibodies against the BPV-1 E2 protein and example 2 discloses the methods used to map Mab 3F12 to SEQ ID No. 1. The specificity of Mab3F12 directed to the peptide fragment of the invention is very high. The antibody 3F12 binds to the peptide (SEQ ID No. 1) even in the presence of high concentration of the salt, for example in the presence of 2M NaCl (FIG. 3). The ability of the antibody to bind specifically under these stringent conditions demonstrates the high affinity of the antibody for its determinant. In addition, the background noise is not observed virtually when the antibody is used in the immunoprecipitation, immunofluorescence and immunoblotting experiments to detect the protein containing the peptide of SEQ ID No. 1. Moreover, if the high background will be a problem, the tolerance of the specific interaction to high concentration of the salt permits to carry out the immunoblotting, immunoprecipitation and immunopurification of the tagged proteins in high-salt buffers to reduce the non-specific binding of the contaminating proteins. In addition, the high salt buffers allow to avoid aggregation of the protein of interest during the purification, if it is necessary.

In the example 3 the peptide tag of the invention is used to detect the protein expression in the transformed bacteria as well as in the transfected eukaryotic cells. The tag can also be used to identify the cellular localization of the fusion protein in the intact cell and to demonstrate the applicability of the tag for identifying the trafficking of the protein through the cellular milieu. For example, one can use the antibodies to SEQ ID No. 1 to test the presence of the fusion protein in the cell lysate or a cell fraction. The antibodies to the tag can be used to test the presence of the fusion protein in a eukaryotic cell supernatant and the methods are known for detecting the antibody binding in intact eukaryotic cells, cell sections, fixed cells or in cell lysates. The antibody can be tagged with the enzyme or other signal system, for example, horseradish peroxidase, or a fluorescent dye. The tag can also be used as a marker for quantifying the level of the gene expression from a cell. The fusion protein can be quantified based on Western blotting from a dot blot or a gel or through the use of immunoassays, for example ELISA assay using antibodies to the tag.

The tag can be incorporated into the protein in various positions along the nucleic acid sequence to determine which portions of the particular protein are necessary for the protein expression or necessary for the particular protein function.

The tag also functions as a binding site for the column chromatography and the protein separation experiments. The use of the antibody to the tag provides the rapid method for identifying, isolating, purifying and quantifying the amount of the fusion protein. The antibody to the tag can be affixed onto sepharose or other beads suitable for the column separation. The sample containing the chimeric protein is passed over the column containing the sepharose beads, or the binding is performed in batch by the end-over-end mixing, and the fusion protein having the tag is bound to the beads coupled by the specific antibody. It is followed by series of washes, the protein is eluted from the column using the standard elution techniques or the expression and/or the function of the fusion protein is studied by the matrix-attached tagged protein. The example of the use of the peptide tag of the present invention to facilitate protein purification is provided in Example 4.

The invention can be better understood by way of the following examples which are representative of the preferred embodiments thereof, but which are not to be construed as limiting the scope of the invention.

EXAMPLE 1

Generation of Mab 3F12

For structure and functional studies of the viral E2 protein, a panel of Mabs was generated against the purified functionally active Bovine Papillomavirus type 1 E2 protein (Kurg et al., J. Virol. 73:4670-4677, 1999). Female BALB/C mice were immunized with 50 μg of BPV1 E2 protein expressed bacterially and purified by conventional methods (Sedman et al., J. Virol. 71:2887-2896, 1997) five times with intervals of 3 to 4 weeks. Following the final injection, the mice were allowed to rest for 5 weeks and then were injected with 100 μg of the antigen. One week later, the final boosts with 100, 200, and 200 μg of protein in PBS were performed at 4, 3 and 2 days before fusion, respectively. Sp2/0 myeloma cells and the cells from one third of the spleen were washed three times with sterile PBS. The final pellet was mixed by tapping the tube, and 1 ml of 50% polyethylene glycol (PEG) 4000 (Merck) was added over 1 min with gentle shaking. The cells were centrifuged at 100 g for 5 min, the PEG solution was removed, and the resuspended cells were plated on five 96-well microtiter plates containing hypoxanthine-aminopterin-thymidine medium. Supernatants were tested 10 days after fusion by direct enzyme linked immunosorbent assay (ELISA).

The hybridoma cell lines were screened by indirect ELISA using the E2 protein as an antigen. The murine hybridoma clone, designated as 3F12, was isolated by screening for the monoclonal antibody capable to bind specifically and with very high affinity to the viral E2 protein. The Mab was purified from the mouse ascitic fluid by ammonium sulfate precipitation and ion-exchange chromatography on Blue DEAE-Toyopearl 650S with a Pharmacia standard chromatography system (Juronen et al., J. Immunol. Methods 136:103-109, 1991).

EXAMPLE 2

Identification of Epitope of BPV-1 E2 Protein by Monoclonal Antibody 3F12

Mab 3F12 showed strong binding activity to the E2 protein in Western blot analysis. To identify the location of the peptide fragment recognized by Mab 3F12, the reactivity of the monoclonal antibody to truncated E2 proteins was determined by Western blot analysis (FIG. 1). The truncated E2 proteins were generated by PCR with appropriate oligonucleotide primers containing either the initiation methionine codon or the terminal recognition codon, and were cloned into the pCG vector containing the cytomegalovirus (CMV) promoter (Kurg et al., J. Virol. 13:4670-4677, 1999). These E2 expression constructs were transfected into COS-7 cells growing in Dulbecco's modified Eagle medium supplemented with 10% fetal calf serum (FCS). The cells from one 60-mm diameter dish were lysed 36 h after electroporation and in 200 μl of Laemmli sample buffer and were analyzed by Western blot analysis. The linear epitope for Mab 3F12 was mapped in the region between residues 184 and 210 of the BPV1 E2 protein. Next, four overlapping peptides covering the region between amino acids 162 and 210 of E2 were synthesized as described in (Langel et al., Int. J. Peptide Protein Res. 39:51 6-522, 1992). The surfaces of the microtiter wells (Maxisorp; Nunc, Roskilde, Denmark) activated with 0.25% glutaraldehyde in PBS were covered with the peptides. The plates were washed with PBS, blocked with 1% non-fat dry milk in PBS/T and then, the 3F12 antibody, diluted in PBS/T was added to the wells. The ELISA analysis showed that the Mab 3F12 was able to bind the synthetic peptide DRVYAGVSSTSSDFR DFPD (amino acid residues 192-210) (SEQ ID No. 5). To narrow down the size of the epitope the additional peptide, GVSSTSSDFRDR (aa 199-208) (SEQ ID No. 2), was synthesized and confirmed by an ELISA to contain the recognition sequence for 3F12 antibody.

To verify that the peptide GVSSTSSDFRDR (SEQ ID No. 2) is the principal determinant for the binding of Mab 3F12 and to map the epitope for the monoclonal antibody 3F12 more precisely, the oligonucleotides coding for the peptide tags with different length and amino acid composition were synthesized (FIG. 2). These oligonucleotides were cloned in-frame in front of the DNA binding domain of the BPV1 E2 protein (aa 310-410) in the pCG expression vector and the resulting expression constructs were transfected into COS-7 cells, and the lysates of the cells were analysed by immunoblot analysis as described above. The results suggested that Mab 3F12 epitope consists of 10 amino acid residues, SSTSSDFRDR (SEQ ID No. 1). All these 10 amino acids are required and are sufficient for strong interaction with the monoclonal antibody 3F12.

EXAMPLE 3

Application of the Peptide Tag in Monitoring of the Recombinant Proteins

We have expressed different proteins using the epitope tag of the invention. In all the experiments, we were able to generate the functional epitope tag, which could be detected by the immunological methods, such as western blotting, ELISA, immunoprecipitation or immunofluorescence microscopy. We have been able to utilize the peptide tag of the invention in a variety of the expression systems and hosts, including *E. coli* and the mammalian cell lines, such as COS-7, Saos-2, CHO, HeLa cells. The cross-reactive proteins have not been detected in any of the host systems tested. Moreover, the sequence homology search of public protein data banks revealed no protein including the sequence SSTSSDFRDR (SEQ ID No. 1). In the tagging experiments, the peptide tag has been placed at the N-terminus, at the C-terminus, or in the middle of the sequence of the recombinant protein. Our results indicate that the peptide tag of the invention is a strong antigenic determinant, which can be utilized adjacent to a variety of flanking sequence environments without significant loss of the antigenicity.

The XylS protein, the transcriptional activator from the TOL plasmid pWWO of the soil bacterium *Pseudomonas putida* has been monitored and purified using the peptide tag GVSSTSSDFRDR (SEQ ID No. 2) (Kaldalu et al., J.

Bacteriology 182:1118-1126, 2000). This protein does not tolerate high level of the over-expression and is prone to aggregate both inside the cell as well as in the solution, in the course of purification (Kaldalu et al., Mol. Microbiol. 20:569-579, 1996). To express the XylS and several truncated variants of the protein at a near to native level in *E. coli*, we constructed vectors for the moderate level of expression of the epitope-tagged fusion proteins. The vectors were based on pBR322, and the tetracycline (tet) promoter of this plasmid was used for expression of recombinant proteins. The vector pBR-3F12 was constructed for the expression of the proteins with N-terminally fused peptide tag GVSSTSSDFRDR (SEQ ID No. 2) recognized by the monoclonal antibody 3F12. We also constructed the vector pBR-NC for the expression of the proteins with the different epitope tags in both N- and C-termini. The N-terminal tag was TTGHYSVRD (SEQ ID No. 6) (recognized by the anti-E2 specific antibody 1 E2) and the C-terminal tag was TSSDFRDR (SEQ ID No. 7), the shorter version of the epitope recognized by Mab 3F12. Vector pBR-3F12 contains XbaI and BamHI sites and pBR-NC XbaI and KpnI sites for the coding sequence, respectively (FIG. 4). The coding sequence of XylS protein, created by PCR, was cloned into these expression vectors. Next, we transformed *E. coli* DH5α with plasmids expressing the tagged versions of XylS and analyzed the expression of the tagged XylS proteins by Western blotting. The Mab 3F12 recognized both 3F12-XylS and NC-XylS proteins, however, the signal was weaker in the case of NC-XylS protein (FIG. 5). This could be explained by the use of the shorter version (TSSDFRDR (SEQ ID No. 7)instead of SSTSSDFRDR (SEQ ID No. 1)) of the 3F12-specific epitope in the double-tagged protein.

For the high-level bacterial expression of N-terminally tagged proteins, we constructed the vector pET-3F12, the derivative of T7 RNA polymerase based on pET-11c vector that contains the tag-encoding sequence and the cloning sites identical to pBR-3F12 (FIG. 4). The coding sequences for the mutant p53 proteins, ΔN39ΔC362 and ΔN61ΔC362 (Lepik et al., J. Virol. 72: 6822-6831, 1998), were cloned into the pET-3F12 vector and were transformed into *E. coli* strain BL21 (DE3). The expression of the tagged p53 protein was monitored by Western blot analysis (FIG. 5). The tag-specific 3F12 and p53-specific pAb240 antibodies were both capable for recognizing the tagged p53 proteins.

For the eukaryotic expression, two coding sequences of the rat glyceraldehyde-3-phosphate dehydrogenase (GAPDH) gene were cloned into pCG-3F12 plasmid (FIG. 4). The pCG vector is the eukaryotic expression vector containing the CMV IE promoter together with the thymidine kinase leader sequence, the SV40 origin of replication and the rabbit β-globin poly A signal (Tanaka and Herr; Cell 60:375-386, 1990). In our work, the 3F12 epitope was fused in frame to GAPDH amino acids 2-333 (pCG-3F12-GAPDH) and the second construct included also the nuclear localization signal of p53 (aa 305-327) fused to the GAPDH protein (pCG-3F12-GAPDH-NLS). Saos-2 cells were transfected with 1 μg of the expression plasmid and analyzed 24 h after transfection. The expression and localization of the proteins were determined by Western blotting and the immunofluorescence analysis, respectively. The 3F12 antibody recognized by both proteins as single bands on the Western blot (FIG. 5) and no cross-reaction with cellular proteins was observed. The immuno-fluorescence staining of the transfected cells with 3F12 antibody indicated that both proteins were localized in the appropriate compartment of the cell: the 3F12-GAPDH in the cytoplasm and 3F12-GAPDH-NLS in the nucleus (FIG. 5). These results indicate that 3F12 epitope-tag can be used for the detection and determination of the localization of the proteins expressed in the eukaryotic cells.

The epitope tags are usually added at the extreme N- or C-terminus of the protein, since the ends of the proteins are more likely to be accessible to the antibody, and the addition of the tag is less likely to affect the function of the protein, and because it is more convenient. However, when the extreme ends of the protein are important for its function or when processing is taking place at these ends, then the internal tagging must be used. Next, we decided to determine whether the 3F12 epitope is recognizable also and usable in the middle of the protein. The cyclooxygenases are the glycoproteins associated with the membranes of the endoplasmic reticulum (ER) and nuclei, and contain the signal peptide in the amino acid sequence, which is cleaved to yield the mature protein. The C-terminus of the protein contains the sequence RDEL, which probably helps to retain the protein in the ER. We inserted the 3F12 epitope into the open reading frame of the cyclooxygenase of Arctic coral into the C-terminal 22-amino acid region (Koljak et al., J. Biol. Chem. 2001, in press). The 3F12 epitope was readily detectable by Western blot analysis of the lysates of the transfected COS-7 cells and by the immunofluorescence analysis of the intact cells (Koljak et al., J. Biol. Chem. 2001, in press). The immunofluorescence staining of the transfected COS-7 cells with 3F12 antibody exhibited signal at the ER and the nuclear membrane, similar to results obtained with the green fluorescent protein (GFP)-tagged Cox and cox-specific antibodies (Trifan et al. J. Biol. Chem. 274:34141-34147, 1999). These results show that 3F12 epitope-tag is usable in the extreme N- and C-terminus as well as in the middle of the protein.

EXAMPLE 4

Application of the Peptide Tag in Purification of the Recombinant Proteins

The XylS protein, a transcriptional activator from the TOL plasmid pWWO of the soil bacterium *Pseudomonas putida* has been purified using the peptide tag GVSSTSS-DFRDR (SEQ ID No. 2)(Kaldalu et al., J. Bacteriology 182: 1118-1126, 2000). This protein does not tolerate the high level of over-expression and is prone to aggregate both inside the cell as well as in the solution, in the course of purification (Kaldalu et al., Mol. Microbiol. 20: 569-579, 1996). The XylS protein was expressed using the pBR-3F12-XylS vector in *E. coli* DH5α cells at 20° C. The cells were harvested at $A_{600}$ of 1.0, washed with TBS and resuspended in 1/10 volume of high-salt lysis buffer containing 100 mM Tris-HCl, pH 7.5, 1.5M NaCl and 5 mM EDTA, 20% (wt/vol) glycerol. Later, CHAPS (0.2%), DTT (10 mM) and the protease inhibitors were added, the cells were incubated with the lysozyme (0.5 mg/ml) on the ice for 20 min and disrupted by sonication. The lysate was clarified by centrifugation at 40 000× g for 30 min. The affinity beads were prepared by coupling 3F12 antibody to divinylsulfon-activated Toyopearl® HW65 TSK-gel (TOSOH, Tokyo, Japan). The 3F12-TSK affinity beads were incubated with the crude lysate at 4° C. for 1 h with the end-over-end agitation. The beads were washed extensively with the high-salt lysis buffer. These 3F12-XylS beads were used for functional-DNA binding and "footprinting" assays.

The invention claimed is:

1. A fusion protein comprising a protein of interest linked to a peptide tag derived from the transactivator protein E2 of Bovine Papillomavirus type 1, said peptide tag being capable of being used in internal tagging and in N- or C-terminus tagging, wherein the amino acid sequence of the peptide tag is selected from the group consisting of SEQ ID NO: 1 and SEQ ID NO:6 and, wherein said fusion protein binds to a high-affinity antibody recognizing said peptide tag.

2. The fusion protein as defined in claim 1, wherein the amino acid sequence of the peptide tag is SSTSSDFRDR (SEQ ID NO: 1).

3. The fusion protein as defined in claim 1, wherein the protein of interest is any native or recombinant polypeptide.

4. The fusion protein as defined in claim 1, wherein one or more linking sequences of amino acids are interposed between the peptide tag and the protein of interest, said linking sequences being cleavable at a specific amino acid by a proteolytic agent.

5. The fusion protein as defined in claim 1, wherein the antibody is the monoclonal antibody 3F12.

6. The fusion protein as defined in claim 1, wherein the antibody has the same binding affinity and epitope specificity as one of the monoclonal antibodies chosen from 3F12 and 1E2.

7. The fusion protein as defined in claim 1, wherein the antibody is chosen from the monoclonal antibodies 3F12 or 1E2, or an antibody having the same binding affinity and epitope specificity as one of the monoclonal antibodies chosen from 3F12 and 1E2; and wherein the antibody is:

a) conjugated to an enzyme or other signal system commonly used, or b) coupled to a solid support.

8. A DNA expression vector comprising a DNA sequence coding for a fusion protein said fusion protein further comprising:

a) a peptide tag being capable of being used in internal tagging and in N- or C-terminus tagging, wherein the amino acid sequence of the peptide tag is selected from the group consisting of SEQ ID NO: 1 and SEQ ID NO:6, b) a protein of interest to be tagged with said peptide tag, and c) optionally at least one linking sequence of amino acids interposed between said peptide tag and said protein of interest, said linking sequence being cleavable at a specific amino acid by a proteolytic agent.

9. A method of producing a fusion protein as defined in claim 1, comprising the following steps:

a) transforming a host cell with the DNA expression vector as defined in claim 8, and b) expressing said fusion protein.

10. The method as defined in claim 9, wherein the host cell is selected from the group consisting of a bacterium, a eukaryotic cell and a mammalian cell.

11. A method of identifying, purifying or isolation the fusion protein of claim 1 using an antibody, wherein the antibody is chosen from one of the monoclonal antibodies 3F12 and 1E2, or the antibodies defined in claims 6 and 7.

12. The method of claim 11, wherein immunoblotting is used to identify the fusion protein.

13. The method of claim 11, wherein immunofluorescence microscopy is used to identify the fusion protein.

14. A method of purifying or isolating the fusion protein of claim 1, wherein affinity chromatography is used to purify or isolate the fusion protein.

15. The fusion protein as defined in claim 1, wherein the amino acid sequence of the peptide tag is TTGHYSVRD (SEQ ID NO: 6).

16. The fusion protein as defined in claim 1, wherein the N-terminus of the protein has a peptide tag according to SEQ ID NO:6 and the C-terminus has a peptide tag of amino acid sequence TSSDFRDR (SEQ ID NO:7).

17. The fusion protein as defined in claim 1, wherein the antibody is the monoclonal antibody 1 E2.

18. The method of claim 11, wherein immunoprecipitation is used to identify the fusion protein.

* * * * *